United States Patent
Volkov et al.

(10) Patent No.: US 10,631,811 B2
(45) Date of Patent: Apr. 28, 2020

(54) METHOD AND SYSTEM FOR PROCESSING OF MEDICAL IMAGES FOR GENERATING A PROGNOSIS OF CARDIAC FUNCTION

(71) Applicants: Dmytro Volkov, Kharkov (UA); Valerij Boyko, Kharkov (UA); Alexander Bakai, Kharkov (UA)

(72) Inventors: Dmytro Volkov, Kharkov (UA); Valerij Boyko, Kharkov (UA); Alexander Bakai, Kharkov (UA)

(*) Notice: Subject to any disclaimer, the term of this patent is extended or adjusted under 35 U.S.C. 154(b) by 1091 days.

(21) Appl. No.: 15/060,970

(22) Filed: Mar. 4, 2016

(65) Prior Publication Data

US 2016/0256059 A1    Sep. 8, 2016

Related U.S. Application Data

(60) Provisional application No. 62/127,937, filed on Mar. 4, 2015.

(51) Int. Cl.
| | |
|---|---|
| *A61B 6/00* | (2006.01) |
| *A61M 5/00* | (2006.01) |
| *A61B 5/055* | (2006.01) |
| *G06T 7/00* | (2017.01) |
| *A61B 8/06* | (2006.01) |
| *A61B 6/03* | (2006.01) |
| *A61B 8/08* | (2006.01) |
| *A61B 5/026* | (2006.01) |

(52) U.S. Cl.
CPC .............. *A61B 6/504* (2013.01); *A61B 5/055* (2013.01); *A61B 6/503* (2013.01); *A61B 6/5217* (2013.01); *A61M 5/007* (2013.01); *G06T 7/00* (2013.01); *A61B 5/0263* (2013.01); *A61B 6/032* (2013.01); *A61B 8/06* (2013.01); *A61B 8/0883* (2013.01); *A61B 8/5223* (2013.01); *A61B 2576/00* (2013.01); *G06T 2207/30104* (2013.01)

(58) Field of Classification Search
CPC combination set(s) only.
See application file for complete search history.

(56) References Cited

FOREIGN PATENT DOCUMENTS

| | | | |
|---|---|---|---|
| JP | WO2010079689 A1 | * | 6/2012 |
| UA | 79099 U | | 4/2013 |
| UA | 82466 U | | 8/2013 |

OTHER PUBLICATIONS

English translation of UA 82466 U, 9 pages.
English translation of UA 79099 U, 6 pages.

* cited by examiner

*Primary Examiner* — Joseph M Santos Rodriguez
(74) *Attorney, Agent, or Firm* — Ware, Fressola, Maguire & Barber LLP

(57) ABSTRACT

A medical diagnostic system includes an image processor to generate a differential frame from two consecutive medical images of the heart based on difference in pixel-by-pixel brightness of the consecutive images. A brightness segmentation image having a plurality of brightness zones is generated based of the differential frame. From the brightness zones, a turbulence index is calculated based on the iso-contour and the area in each brightness zone. The turbulence index is a quantitative representation of a degree of turbulence in the blood flow which can be used to generate a prognosis and/or diagnosis of cardiac function.

20 Claims, 17 Drawing Sheets

| i | U | L | S | K |
|---|---|---|---|---|
| 1 | -7,5 | 944 | 1402 | 7,11 |
| 2 | -2,5 | 3477 | 8047 | 10,93 |
| 3 | 2,5 | 4155 | 15653 | 9,36 |
| 4 | 7,5 | 1081 | 6304 | 3,84 |

(1, 2, 3, 4 = number of iso-contours)

METHOD AND SYSTEM FOR PROCESSING OF MEDICAL IMAGES FOR GENERATING A PROGNOSIS OF CARDIAC FUNCTION

TECHNICAL FIELD

The present invention relates to a method and system for the analysis of cardiac function utilizing processed image data and use thereof in cardiac diagnostic equipment for generating cardiac diagnosis, and particularly to the use of image data to assess the level of turbulence in blood flow.

BACKGROUND OF THE INVENTION

The problem of finding of new methods to assess the functional state of physiological processes, including cardiovascular system, is very important because the number of patients with these diseases increases every year, and that is the leading cause of death among adults. A large number of potential patients require careful identification and diagnosis of these processes in early stages of the disease and determination of the prognosis. Special attention is need for the identification of patients with early stages of chronic disease such as valvular disease, thoracic aortic aneurysm, among others, that could lead to heart failure.

Like any liquid with viscosity, blood during leaking can form complex random braces and flows leading to increased resistance to blood flow and causing turbulence to appear. Usually, the degree of turbulence depends on the viscosity and velocity of the fluid and the roughness of the object walls through which the fluid moves.

In humans and animals, the heart creates a pulsating flow, which spreads to different parts of the cardiovascular system, providing conditions for the continuous mixing of locally available blood with the "new" blood that is delivered with each pulse. The least possible degree of turbulence leads to minimum resistance to the blood flow and creates optimal conditions for effective blood movement and delivery. Thus, in a healthy heart with healthy vessels, blood moves with a relatively laminar flow, and therefore is delivered without creating significant local blood movements. In the case of certain diseases, there are factors that trigger the appearance of increased turbulence.

Currently, the level turbulence in blood flow is assessed qualitatively.

SUMMARY OF THE INVENTION

The present invention is concerned with a method and system for medical diagnostics based on the differential frame of two consecutive medical images of the cardiovascular system derived from the difference in pixel-by-pixel brightness of the consecutive images. Accordingly, the first aspect of the present invention is a medical diagnostic system for a prognostic of cardiac function, comprising:
  an image storage device arranged to store medical images of a cardiovascular system, said medical images including consecutive images, the image storage device comprising a plurality of image frames, the image frames arranged to store pixel-by-pixel brightness of the consecutive images;
  an image processing module arranged to generate one or more differential frames from the plurality of image frames;
  a data processing module configured to provide information indicative of blood flow in the cardiovascular system based at least partly on the differential frames.

According to an embodiment of the present invention, the differential frames are generated based on the pixel-by-pixel brightness of the consecutive medical images, and the image processing module is also configured to generate a brightness segmentation image based on said one or more differential frames.

According to an embodiment of the present invention, the data processing module configured to provide a turbulence index based on the brightness segmentation image, the turbulence index comprising the information indicative of blood flow in the cardiovascular system.

According to an embodiment of the present invention, the data processing module comprises a first data processor configured to compute a contour and an area of the brightness segmentation image, and a second data processor to compute the turbulence index based on the contour and the area of the brightness segmentation image.

According to an embodiment of the present invention, the image processing module is also configured to delineate cavity and wall of the cardiovascular system boundaries based on the differential frames, and the data processing module is also configured to generate information indicative of wall contraction-relaxation strength and synchronicity in the cardiovascular system.

According to an embodiment of the present invention, the image processing module is configured to delineate cavity from walls and walls from cavity and surrounding structures in the cardiovascular system.

According to an embodiment of the present invention, the data processing module is arranged to provide the information to an information display.

According to an embodiment of the present invention, the image storage device is arranged to receive the medical images from a medical imaging device.

According to an embodiment of the present invention, the medical images are X-ray images, computed tomography scan images, magnetic resonance imaging images, ultrasound images, angiography images and the like.

One second aspect of the present invention is a method for generating a prognosis of cardiac function, comprising:
  acquiring a plurality of consecutive images of a cardiovascular system;
  generating a differential frame from at least two of the consecutive images; and
  providing information indicative of blood flow in the cardiovascular system based on the differential frame.

According to an embodiment of the present invention, the method further comprises:
  generating a brightness segmentation image based on the differential frame;
  determining a contour length and an area of the brightness segmentation image; and
  computing a turbulence index based on the contour length and the area for providing the information.

According to an embodiment of the present invention, the turbulence index is computed from the ratio of the contour length of the brightness segmentation image to a circumference of a substantially circular loop having an area substantially equal to the area of the brightness segmentation image.

According to an embodiment of the present invention, each of the images comprises a spatial distribution of pixel-by-pixel brightness levels and the differential frame is generated by comparing the spatial distribution of pixel-by-pixel brightness levels of said at least two of the images.

According to an embodiment of the present invention, the differential frame comprises a range of brightness levels and wherein the range of brightness levels is segmented into a plurality of brightness zones including a max-brightness zone and a min-brightness zone, and wherein the brightness segmentation image is generated from the differential frame based on the plurality of brightness zones after removing the max-brightness zone and the min-brightness zone.

According to an embodiment of the present invention, the method further comprises:
delineating cavity and wall boundaries of the cardiovascular system; and
generating information indicative of wall contraction-relaxation strength and synchronicity based on said delineating and differential frames analysis.

DETAILED DESCRIPTION OF THE INVENTION

Figure 1:
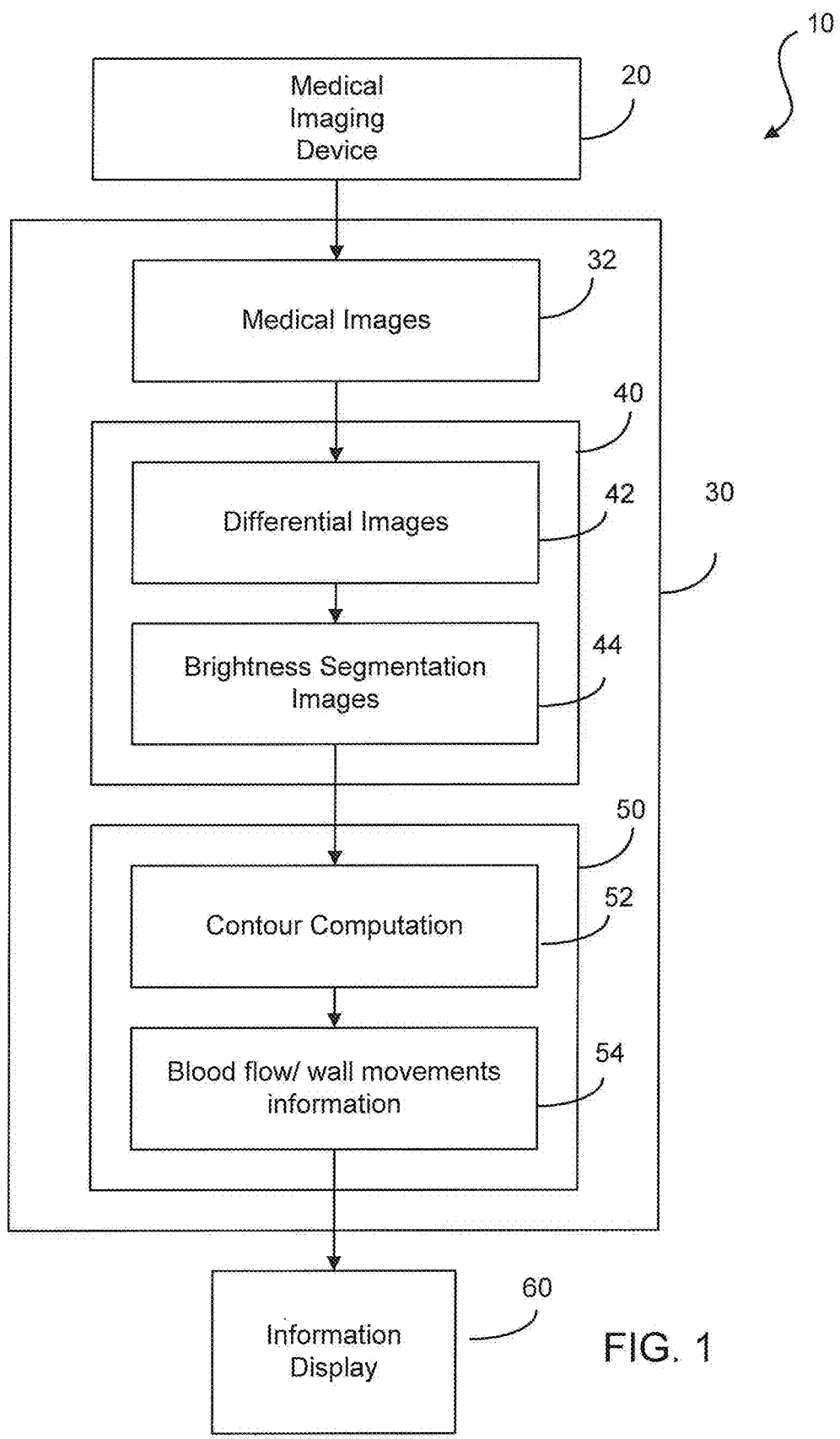
FIG. 1 is a block diagram representing a system for processing image data according to an embodiment of the present invention.

The present invention provides a quantitative analysis of turbulent fluid motion in body vessels. The analysis is based on a series of images after administration of a contrast agent into a cavity of the organ (heart chamber). A frame comparison is carried out by comparing each frame with the subsequent one in order to generate a differential frame of pixel-by-pixel brightness differences between two consecutive frames. From one or more differential frames, a brightness segmentation frame is generated by using isocontours of the brightness levels on the differential frames. Isocontours are created as lines, limiting an area of equal brightness through a range of N sub-levels by using the formula $\Delta=(Umax-Umin)/(N-1)$, where Umax and Umin are maximum and minimum brightness levels, respectively. Here N is a positive integer greater than 2 and can be 5, for example.

Extreme iso-contours, which are equivalent to Umax and Umin, determine the main sensitivity, with the magnitude of $\Delta/2$, being analyzed. By means of the created isocontours, the degree of turbulence is calculate as the ratio of the total length of the contour in selected isocontours to the length of a round object that has an area equivalent to the chosen one as follows: $k_{turb}=L_{obj}/L_{circ}$, where $k_{turb}$—degree of turbulence or the turbulence index; $L_{obj}$—total length of the contour in studied isocontours group; $L_{circ}$—length of the round object contour, which is assumed to be equal to the square root of $4\pi \times S_{circ}$, where $S_{circ}$ is area of the equal round object set to be equal to $S_{obj}$ or the area of studied isocontours.

Creating a series of differential frames allows analyzing not the primary frames, but the differential frames received as the per pixel difference of two consecutive frames of conventional standard diagnostic frames of a film loop. In other words, the differential frame is computer generated as a digital frame, with each point at which there is a difference in brightness of two homologous identical points of consecutive frames. The generated differential frames can highlight changes in the fluid input process. For example, during ventriculography, the dynamics of native "pure" blood propulsion through the mitral valve to the left ventricle are clearly identified, filled with a mixture of blood and contrast agent.

A comparison of performance of each previous frame with the following, in turn, allows removing, at that moment, any motionless components from incoming frames on differential frames and thereby clearly identifying the dynamic components in the resulting differential frames that emphasize changes in the input process.

Ejection of contrast agents into the blood bodies (mainly veins, such as ejection of contrast to cubital vein) avoids further intervention to the investigational organ (e.g. heart) using a catheter and thereby reduces the trauma and the risk of complications.

A method of differential frame processing using isocontours (lines that limit objects of equal brightness) for a series of consecutive frames allows calculating the change in the degree of turbulence. Since slices of brightness on several levels are of interest, it is necessary to build more groups of isocontours to increase the accuracy of the assessment of degree of turbulent flow.

The level of turbulence, among other intracardiac blood flow characteristics, can provide a new digitized, numeric, simple and appropriate global determinant of cardiac function. The preliminary data from a small group of patients' clearly shows that the worse the heart function, the higher the level of turbulence that is present, but that data was taken with patients with an obvious heart failure situation and also reduced ejection fraction. Patients which would have a normal state and a normal ejection fraction, but with a high level of turbulence are believed to be at a greater risk to develop heart failure with time, and so the inventors determined that the level of turbulence can be accurate enough to provide a prediction of future heart failure.

This situation is more likely to occur with so-called diastolic heart failure in which there is a stiff myocardium, with no pumping function reduction, but morbidity and mortality is equal and some of these patients would have deterioration of pumping function with time. Having such data would permit a health care provider to take steps in advance to reduce the risk of heart failure, knowing that prophylaxis is better than treatment.

The system and method according to the present invention also can also be used in assessing the efficacy of different therapies including cardiac resynchronization therapy, valve replacement etc. possibly including drug therapies, using a before and after analysis of the level of turbulence, and also as a simple, non-invasive manner to monitor and log information on heart function of a patient over time, to develop a quantitative history of cardiac function.

The present invention utilizes an analysis of a series of images. The images can be obtained from diagnostic equipment such as are obtained via ventriculography, for example, and then generating a set of differential slides. The blood flow turbulence level corresponding to a level of cardiac function is calculated. Based on the result, a prognosis as to the likelihood of heart failure development is then made. Once generated, a health care provider can take steps to address the likelihood through treatment options or other means based on the output from the system.

The present invention can be carried out in a medical diagnostic system such as the system 10 as shown in FIG. 1. As seen in FIG. 1, the system 10 includes a core processing module 30, which is arranged to receive medical images from a medical imaging device 20. The core processing module 30 comprises an image storage device 32 arranged to store the medical images obtained from the medical imaging device 20. For example, the image storage device may comprise a plurality of image frames, which are arranged to store pixel-by-pixel brightness of the medical images. Electronic signals indicative of the pixel-by-pixel brightness of the medical images are provided to an image processing module 40 for process the pixel-by-pixel brightness of the consecutive medical images into a brightness segmentation image. Electronic signals indicative of the brightness segmentation image is provided to a data processing module 50 in order to compute a turbulence index based on the brightness segmentation image for prognostic of cardiac function. For example, the turbulence index can be displayed on an information display 60 so that a health care provider can takes to address the likelihood through treatment options based on the turbulence index.

As seen in FIG. 1, the image processing module 40 may comprise a first image processor 42 configured to generate a differential image frame based on the pixel-b-pixel difference of brightness between at least two of the consecutive images; a second image processor 44 configured to generate the brightness segmentation image based on the differential image frame. The data processing module 50 may comprise a first data processor 52 configured to compute a contour (iso-contour) and an area of the brightness segmentation image which is segmented from a differential image based on brightness zones; and a second data processor 54 configured to generate blood flow/wall movements information such as the turbulence index based on the contour and the area of the brightness segmentation image and the information indicative of wall contraction-relaxation strength and synchronicity based on the delineation of cavity and wall boundaries of the cardiovascular system and the differential frames analysis. The medical images obtained medical imaging device 20 can be X-ray images, computed tomography (CT) scan images, magnetic resonance imaging (MRI) images, ultrasound images, angiography images, etc.

Accordingly, the generation of a prognosis of cardiac function can be carried out in the following steps:
acquiring a plurality of images of a cardiovascular system;
generating a differential frame from at least two of the images;
generating a brightness segmentation image based on the differential frame;
determining a contour length and an area of the brightness segmentation image; and
computing the turbulence index based on the contour length and the area of the brightness segmentation image.

According to an embodiment of the present invention, the turbulence index is computed from the ratio of the contour length of the brightness segmentation image to a circumference of a substantially circular loop having an area substantially equal to the area of the brightness segmentation image, wherein each of the images comprises a spatial distribution of pixel-by-pixel brightness levels and the differential frame is generated by comparing the spatial distribution of pixel-by-pixel brightness levels of said at least two of the images.

According to an embodiment of the present invention, the differential frame comprises a range of brightness levels and wherein the range of brightness levels is segmented into a plurality of brightness zones including a max-brightness zone and a min-brightness zone, and wherein the brightness segmentation image is generated from the differential frame based on the plurality of brightness zones after removing the max-brightness zone and the min-brightness zone.

To facilitate the understanding of the present invention, real medical images are used to demonstrate some of the steps in the turbulence index generation.

Figures 2A, 2B, 2C:
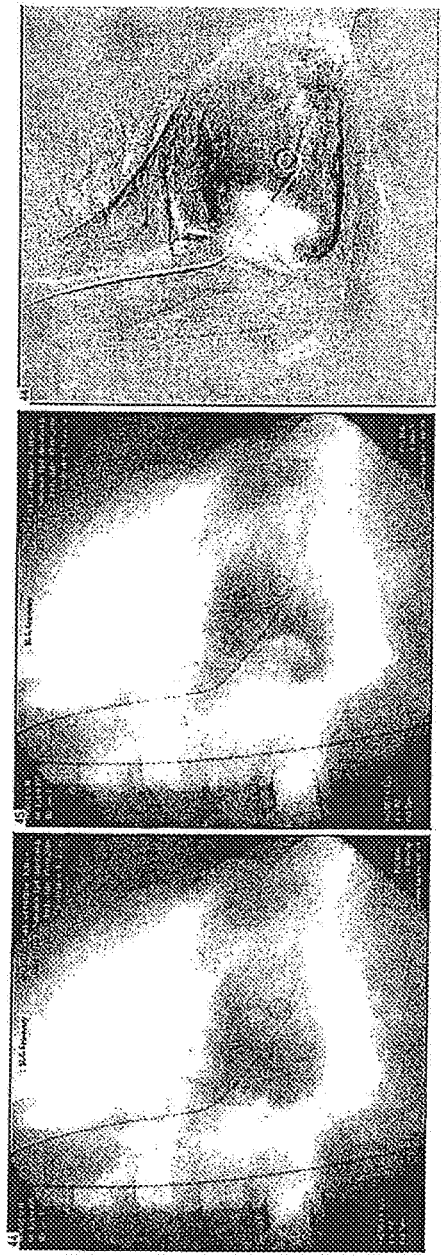
FIGS. 2A and 2B show two consecutive frames of conventional ventriculography.
FIG. 2C shows a differential frame generated from the images of FIGS. 2A and 2B.

FIGS. 2A, 2B and 2C show how a differential image is generated. FIGS. 2A and 2B are two consecutive (pixel-by-pixel brightness) frames of conventional ventriculography, and FIG. 2C is a differential frame. As seen in FIG. 2C, the left ventricle is full with contrast, indicating of incoming "fresh" blood which appears as white cloud.

Figure 3:
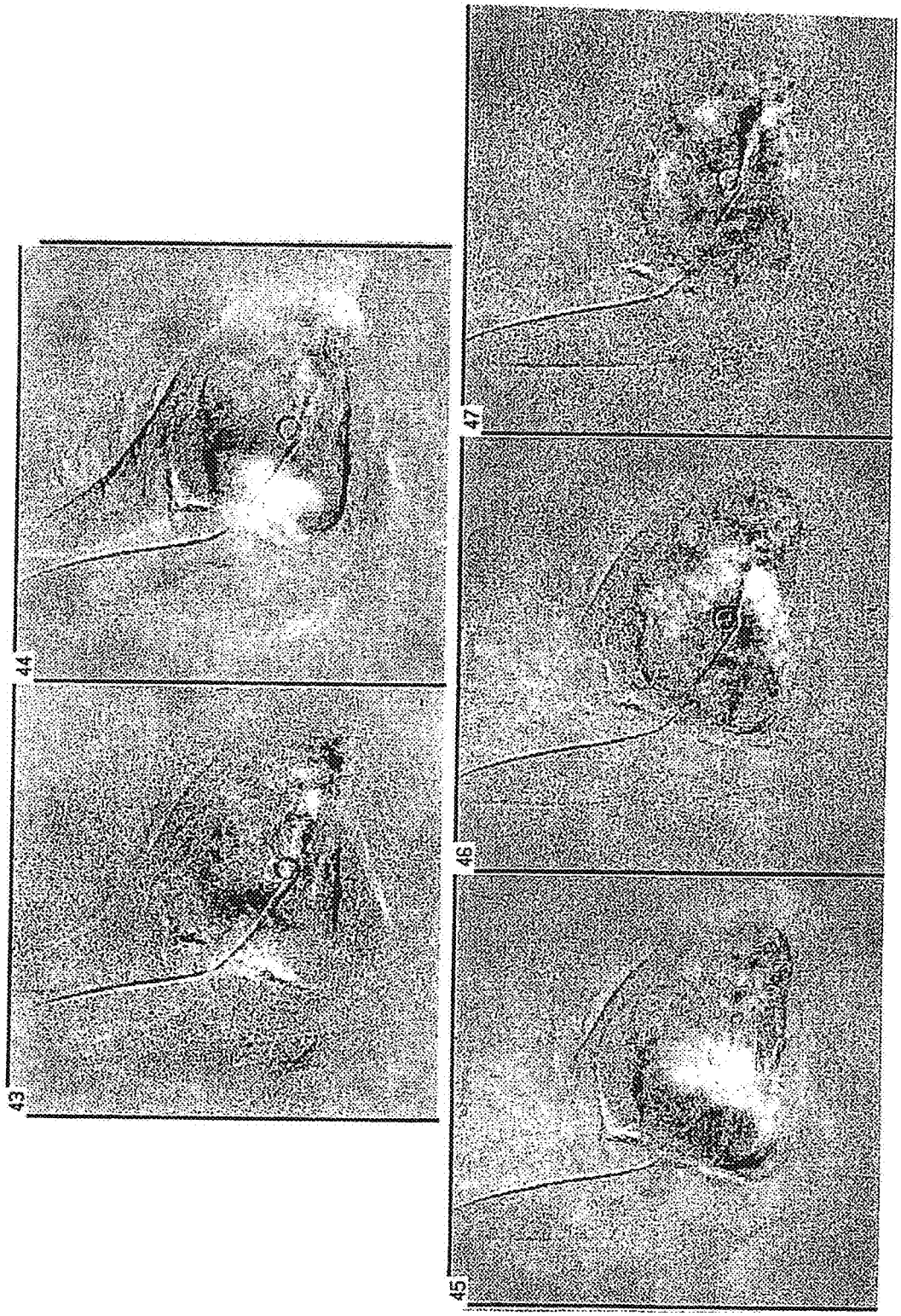
FIG. 3 shows a series of consecutive differential frames.

FIG. 3 shows a series of consecutive differential frames, showing detailed information about intracardiac blood flow.

Figure 4:
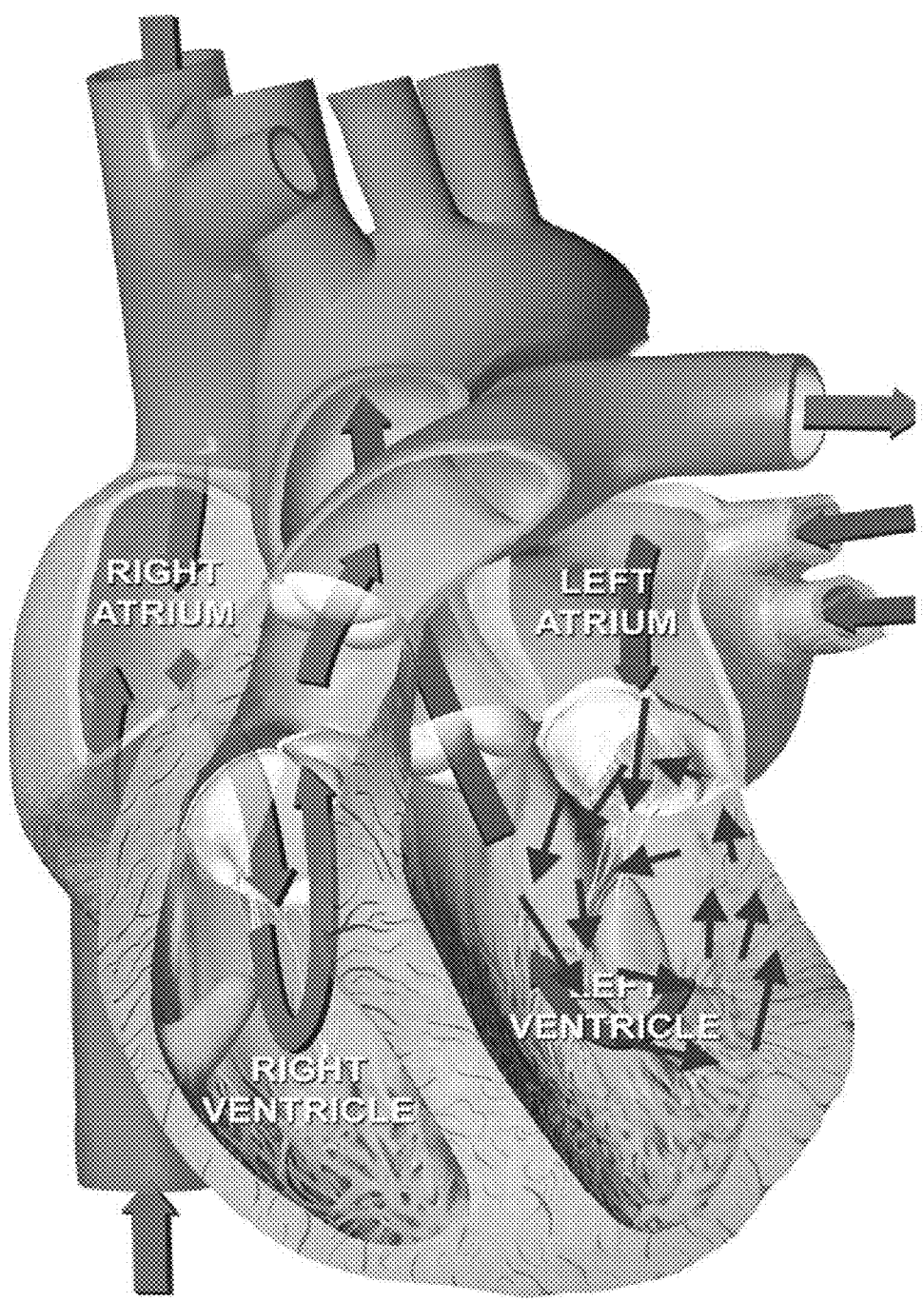
FIG. 4 is a graphical representation of a heart.

The differential frame can be generated using pixel-by-pixel differences between two conventional consecutive slides of a conventional contrast study which involves injecting contrast liquid by a catheter into a left ventricle (see FIG. 4), usually done to distinguish a hear silhouette edge and make calculations of the ejection fraction and on moving dynamics abnormalities of the ventricle.

Figure 5A:
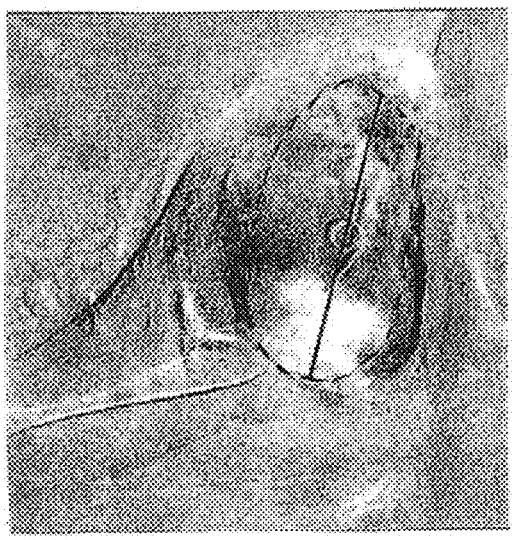
FIG. 5A is a differential frame of the left ventricle with a ROI established thereon.
Figure 5C:
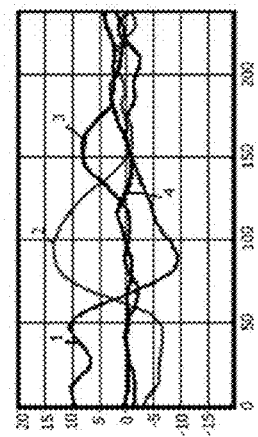
FIG. 5C is a graph showing the result of brightness calculation.
Figure 5B:
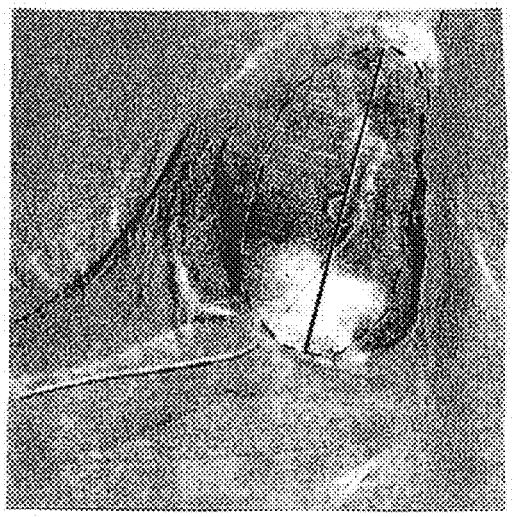
FIG. 5B is the same different frame having a series of straight lines for brightness calculation.

The blood dynamics in or the blood propulsion through the left ventricle are demonstrated in FIGS. 5A-5C. FIG. 5A is a differential frame in which a region of interest (ROI) is established. The ROI is bound by a dashed loop around a solid basal line along which the blood flow is analyzed. Within the ROI, a series of straight lines perpendicular to the basal line are formed (FIG. 5B) and the average brightness along the straight lines is calculated as a brightness integral divided by its length. FIG. 5C shows the result of the calculation. In FIG. 5C, brightness is on the ordinate axis and pixel distance is the abscissa. The four curves (1, 2, 3, 4) in FIG. 5B represent when one, two, three or four consecutive slides are analyzed.

The maximum brightness moves along the left ventricle, becoming of lower intensity, that is, more gray as blood mixes with the contrast medium. In normal hearts, this process is brisk, quick and less-mixing—the colors are more black and white but not gray, while in failing hearts, the speed of propulsion is lower and the spectrum is more gray, with a low dispersion of brightness.

One of the most important features of the present invention is the determination of a turbulence level, which provides a quantitative indicator of cardiac function.

Figure 6A:
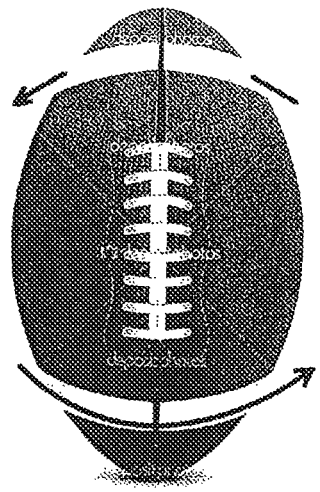
FIGS. 6A and 6B show different rotations of a rugby ball.
Figure 6B:
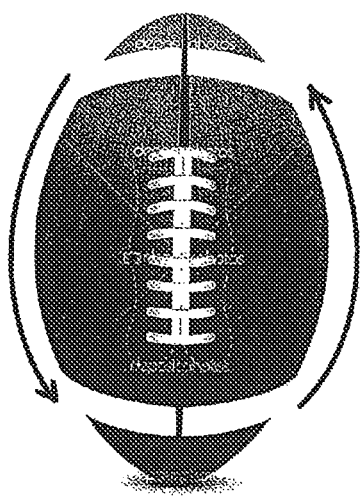

In situation with contrast ventriculography, the left ventricle is filled with contrast liquid in which "new" blood from the left atrium comes through the mitral valve. The two liquids have different viscosity and roentgen opacity so they become mixed up when some level of turbulence is present. In the ideal situation, the coming blood will behave like a rugby ball, and have an elliptical shape, quickly prolapsing to the left ventricle, moving and adapted in the apex and pulled out to the aorta. It is very crucial to have this ball rotated around its long axis to alleviate grabbing (FIG. 6A). If it is rotated in a perpendicular orientation, it is very difficult to catch (FIG. 6B). The same is in the left ventricle—the walls are better at accepting such coming blood, even making some circumflexion movement to facilitate and enhance blood protrusion. But if it is moving in another way, it will create increased turbulence and worsen heart function, making the heart more round-shape instead of elliptical.

Figure 7A:
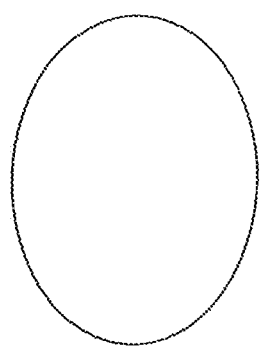
FIGS. 7A-7C are graphical representations of the blood flow.
Figure 7B:
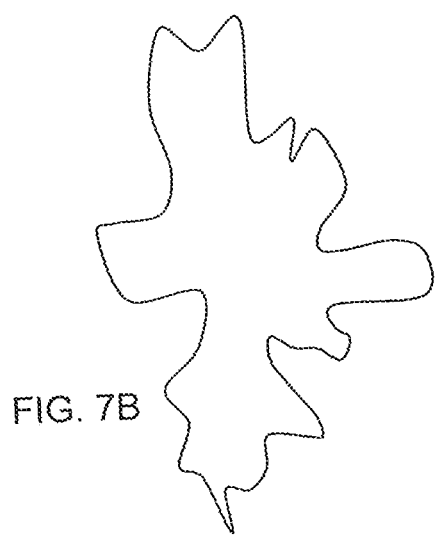
Figure 7C:

As seen in FIG. 5A, new blood comes to the left ventricle with a quite smooth surface (FIG. 7A), then it becomes another shape by moving further into the ventricle and being mixing up with the rest of the blood (e.g. contrast). Note that the boundary has a more intended cutting edge (FIG. 7B), known in mathematics as being "fractal" and then it can disintegrate into several objects if the level of turbulence is very high (FIG. 7C).

During a cardiac cycle, some stable amount of blood enters the chambers during diastole. Normally the ball of coming blood has less fractality and is compact, but in heart failure, it early becomes disintegrated and fractal.
Equation To quantify the degree of turbulence ($k_{turb}$), we use the simple exponent $k_{turb} = L_{obj}/L_{circ}$, i.e. ratio of the actual total length of the boundary of the object ($L_{obj}$) to the length of the circumference of the virtual circular object having the same area, or $L_{circ}$. The quantity $k_{turb}$ is hereafter referred to as a turbulence index.

If $k_{turb}=1$, then there is no turbulence. With an increasing level of turbulence, $k_{turb}$ increases.

This method of analysis is applied to the differential frames to extract a quantitative level of blood turbulence.

In the normal heart, the blood moves more or less laminar. In the case of certain diseases, factors appear which generate turbulence.

Figures 8, 17:
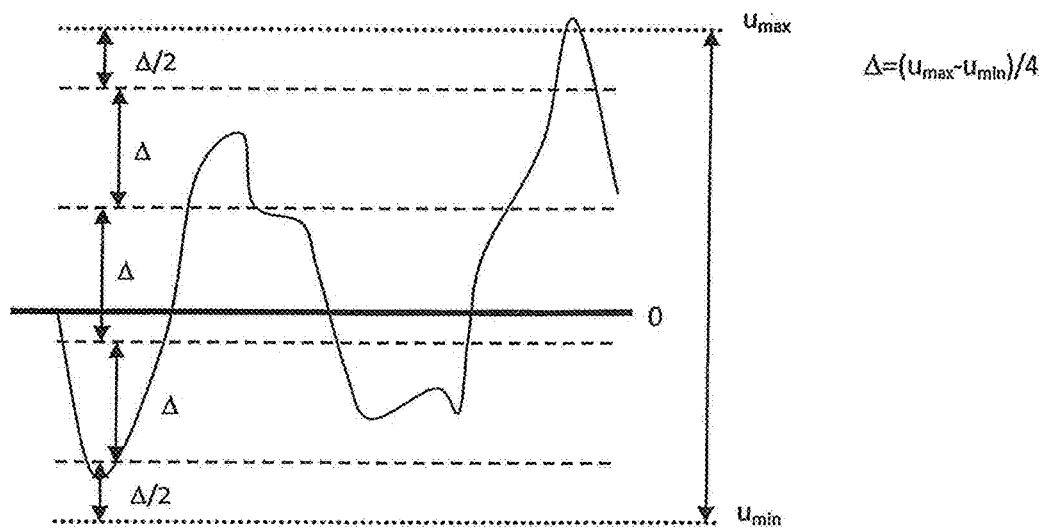
FIG. 8 is a graph showing how iso-contour zones are determined.
FIG. 17 is a table showing the turbulence indices with different number of iso-contours.

Information is available in consecutive image frames that can provide data on the degree of turbulence in blood flow.
Isocontours The actual calculation of the turbulence index using that equation involves dividing the whole brightness spectrum of the moving blood into several "isocontours", which are the lines which delineate areas with equal brightness. One method involves the computer based program delineating 5 zones, by the method shown on FIG. 8. Of special interest are the extreme zones with white and black colors, and central "gray" zones which reflect mixing of blood and may be of interest for the amount of "pooling" that occurs of deposited blood. In general, the relative minimum and maximum brightness are dependent upon common distribution of white and black levels and that is why the distribution is not symmetrical to zero as shown in FIG. 8.

As the brightness range of a differential image (frame) is divided by five iso-contour zones ($\Delta$) with $\Delta=(Umax-Umin)/4$, the differential image is effectively segmented into five zones to become a brightness segmentation image.

Figure 9:
FIG. 9 shows a brightness segmentation image having iso-contours thereon.

FIG. 9 gives a presentation of iso-contours on a brightness segmentation image. Some iso-contours can be seen in the image. An iso-contour is a boundary of portion of the image, delineating two different brightness zone.

It has been found that, with a limited number of patients, the turbulence index $k_{turb}$ in near 2 in at least a relatively healthy heart. Cardiac diseases with heart failure are increased with a $k_{turb}$ of 4 or more.

In addition to assessing the degree of turbulence in separate frames, the system and method can determine a rate of change (increase) of fractality in a series of consecutive frames during a cardiac cycle, which may also have prognostic value.

It is important that with the increasing resolution of diagnostic equipment, the accuracy of measurements make possible the creation of a three-dimensional map of turbulence.

Figure 10A:
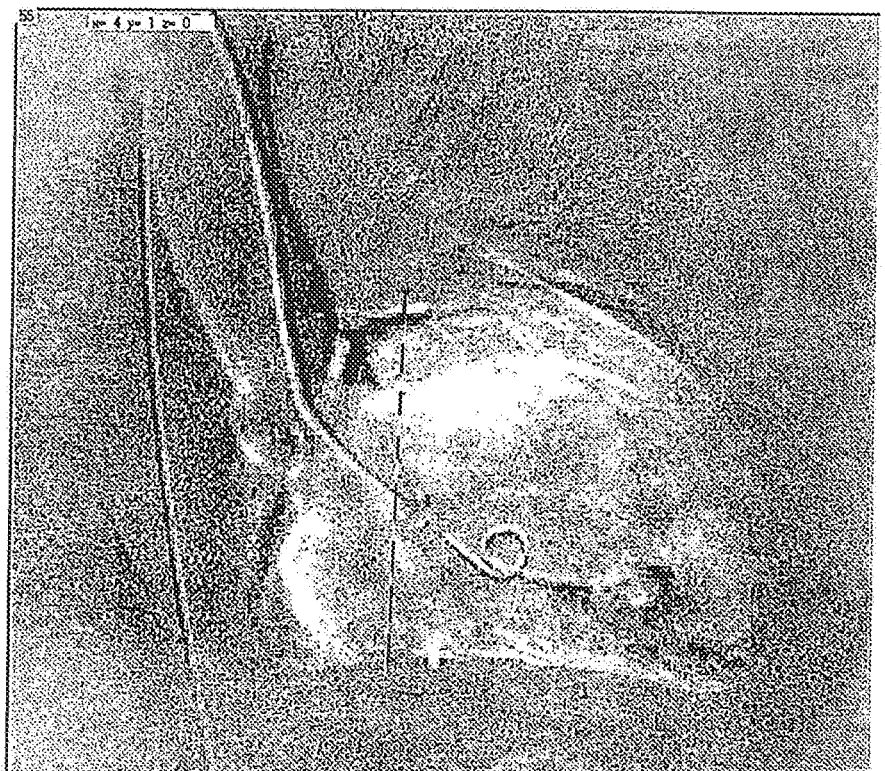
FIGS. 10A and 10B are two differential frames with a pre-specified line for evaluation of heart wall movements.
Figure 10B:
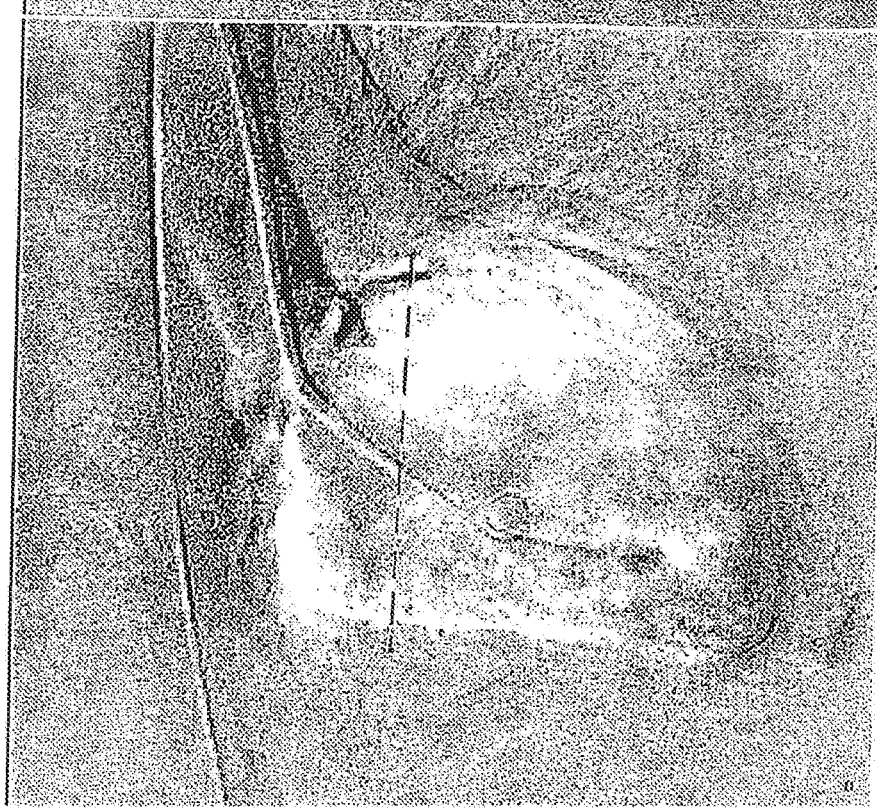
Figure 10C:
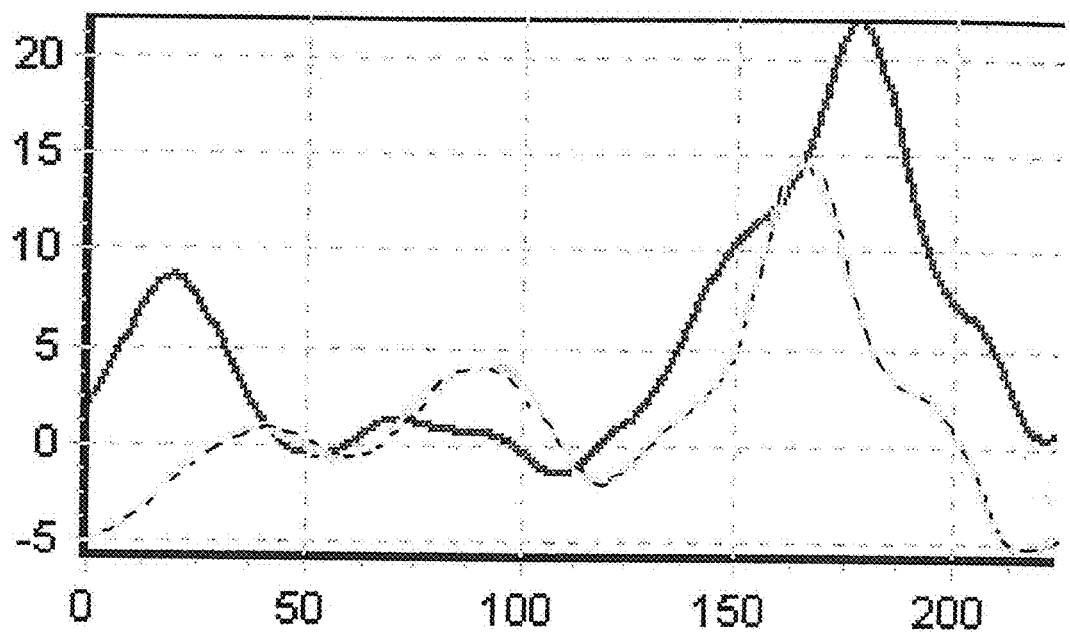
FIG. 10C is a graph showing the brightness distribution related to heart wall movements resulting from the evaluation in normal and failing hearts.

One more measurement included in the present invention is a brightness distribution along the pre-specified line. This may be used for evaluation of wall movements (FIGS. 10A-10C). Heart wall movements on differential slides can be seen clearly as black and white shadows alongside the cardiac silhouette during diastole and systole.

Figure 11C:
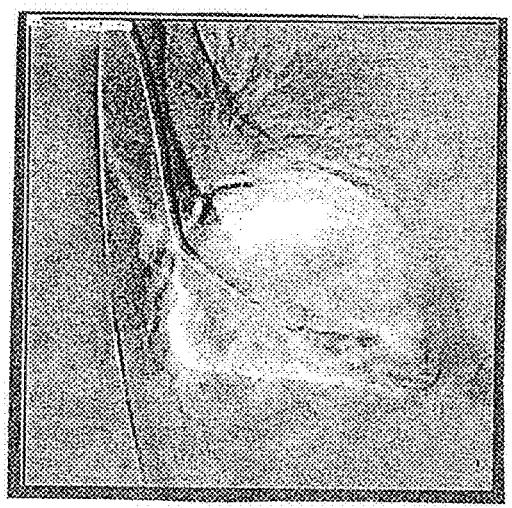
FIGS. 11A-11C show variants in heart wall contraction.
Figure 11A:
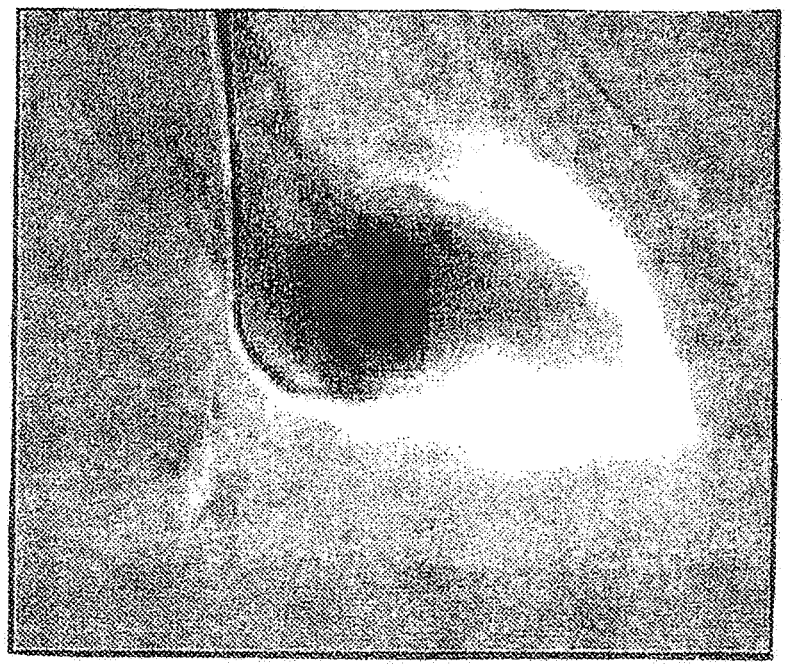
Figure 11B:

For example, FIGS. 10A and 10B are two consecutive differential slides or frames. A line (dashed line) is established to investigate wall movements in two consecutive differential slides. FIG. 10C is a graph of brightness (+5 to +20) alongside the line (distance in pixels 0-200) from each of FIGS. 10A and 10B. With normal contraction of the heart, the shadows look like thick homogeneous layers of similar color or gray-level (FIGS. 11A and 11B). With impair function, these layers become thinner and inhomogeneous (FIG. 11C).

Figure 12A:
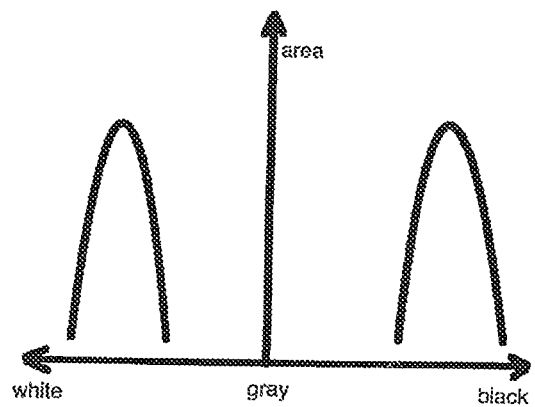
FIGS. 12A and 12B are graphical representations of a normal heart wall contraction and an impaired wall motion.
Figure 12B:
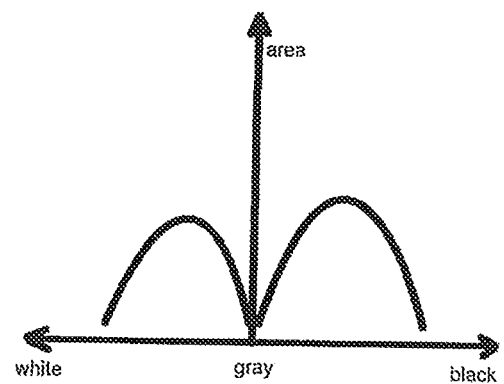

In this context it would be useful to calculate and generate a report on the distribution of wall brightness during one cardiac cycle. With a normal contraction, it should have two distinct peaks of white and black color reflecting synchronized wall motion (FIG. 12A). In impaired and disconcordant wall motion, this peaks would be more sloping, closer to a gray zone (FIG. 12B).

The data after further processing could be presented in a simple numeric mode, easily reflecting global contraction and relaxation strength, balance and synchronicity. Potentially the slopes of these curves could be predictive for further prognosis of heart's contraction efficiency and heart failure progression.

Figure 13:
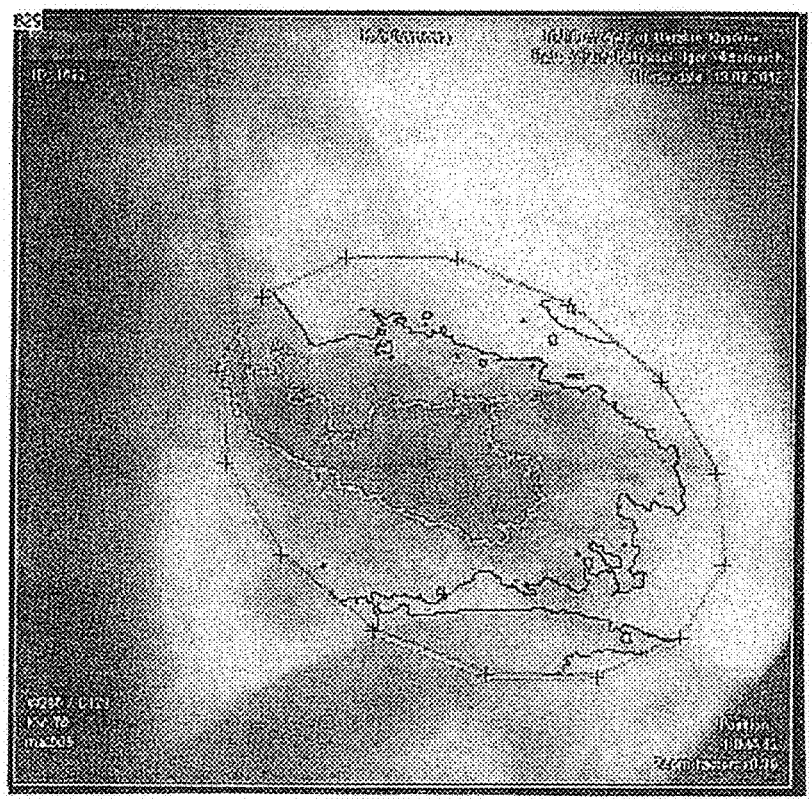
FIG. 13 shows how ROI can be adjusted to enhance the iso-contours.
Figures 14A, 14B:
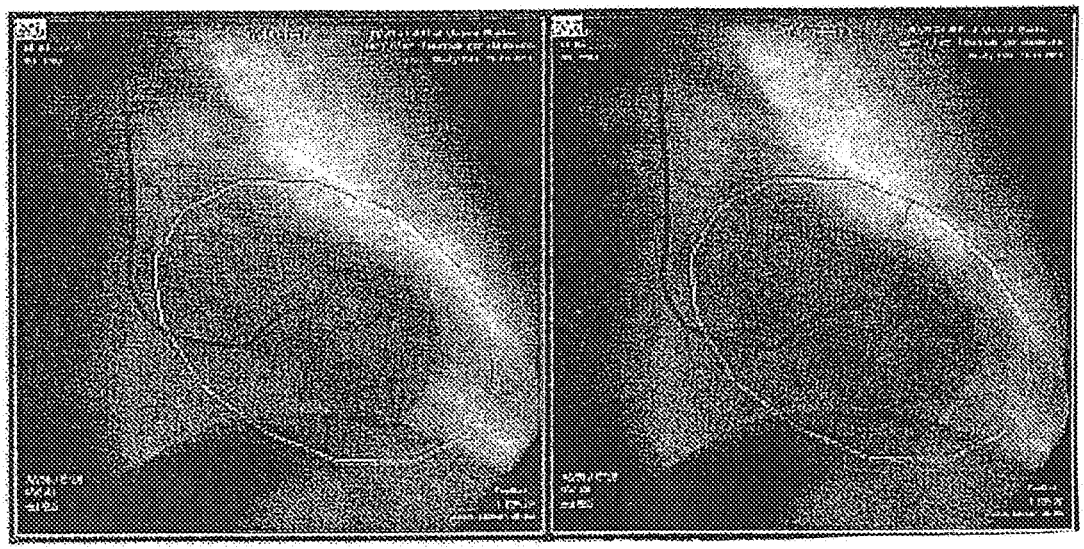
FIGS. 14A and 14B show the optic flow in two consecutive differential frames.
Figure 14C:
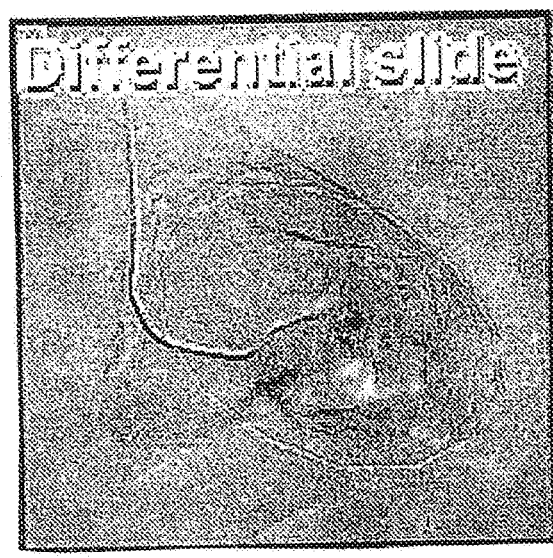
FIG. 14C is a differential slide showing the contrast in optic flow between FIGS. 14A and 14B.
Figure 15:
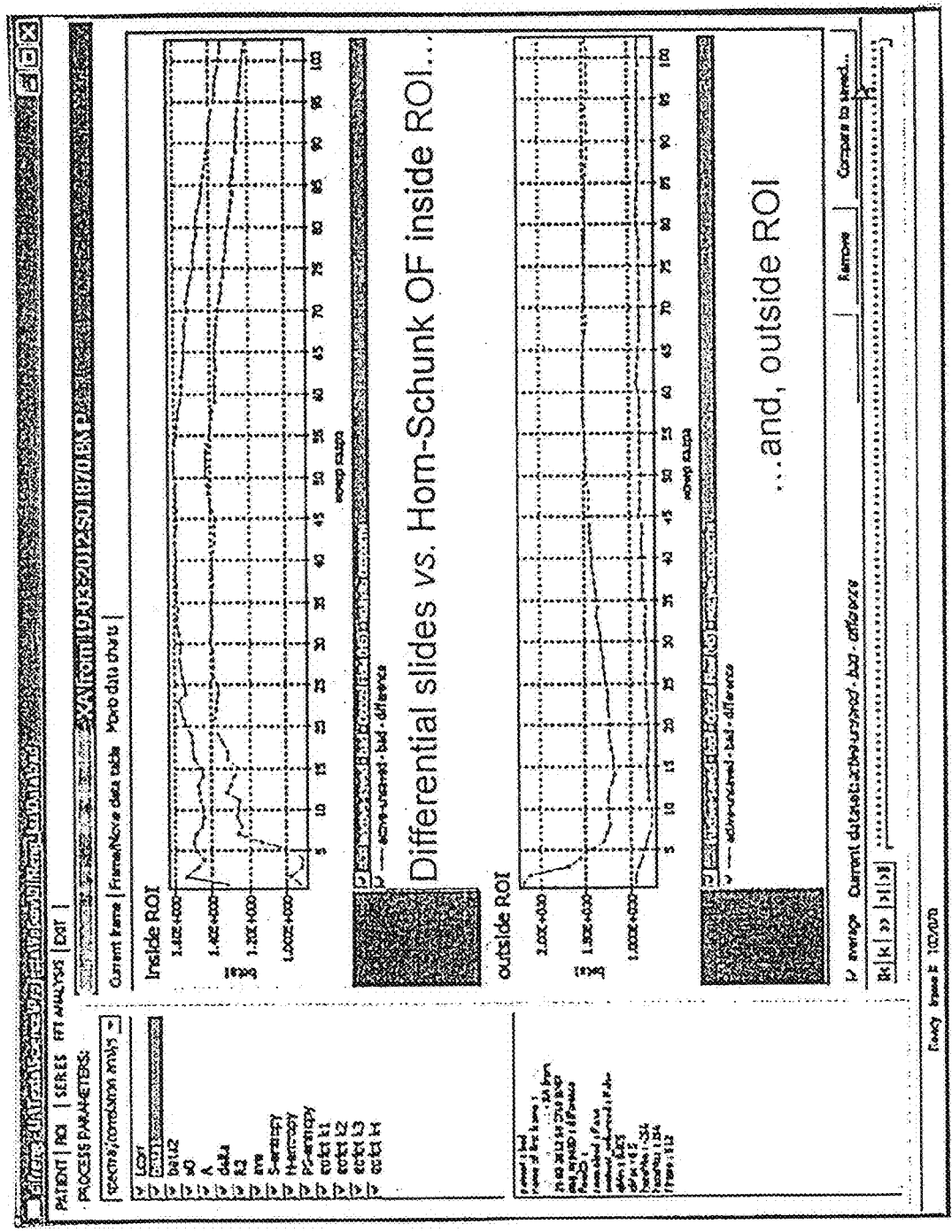
FIG. 15 is a graph showing different methods for turbulence evaluation.

In an embodiment of the present invention, several enhancements and additional potential for performing more sophisticated mathematical and statistical analysis, including more precise iso-contours management of the regions of interest. For example, the region of interest (ROI) can be adjusted to better define the iso-contours as shown in FIG. 13. Optic flow can be calculated between two consecutive differential frames (FIGS. 14A and 14B). The contrast between these two consecutive differential frames is shown in FIG. 14C. Furthermore, turbulence evaluation can be carried out in different methods. For example, Hom-Schunk optic flow inside ROI and outside ROI can be computed so as to compare these optic flows to the differential slide as shown in FIG. 15. Furthermore, advanced spectrum of diagnosis indexes can be searched in order to distinguish a "good" patient over a "bad" patient.

In summary, the essence of the differential technique is to analyze not original frames, but differential frames generated from the per pixel difference between two normal standard frames. Thus differential frame are created as a frame displaying each point at which there is a difference in brightness between two homologous points of consecutive frames. Iso-contour levels are created by highlighting the relative maximum and minimum brightness, depending on the total value of "bright" and "dark" areas, and therefore do not reflect the actual maximum and minimum value and are asymmetric with respect to zero. The entire range is divided into 5 sublevels separated by a distance $\Delta$, where $\Delta=(Umax-Umin)/4$, where Umax and Umin—maximum and minimum brightness value, respectively. The central level as the "gray" area is not informative and is not analyzed, nor are extreme isocontours which have levels of $Umax-\Delta/2$ and $Umin+\Delta/2$. Quantitative assessment of the turbulence degree is carried out based on the ratio of the total length of a boundary of a selected group of isocontours to a circumference of an equivalent round object that has the same area as the chosen group, that is, to an area that would have essentially no turbulence. If this ratio is close to one, turbulence is absent. With increasing turbulence—the ratio increases, as the increased fracturing enlarges the boundary.

Thus, the method of creating the line, limiting areas of equal brightness (iso-contours), by which the degree of turbulence then be calculated as the ratio of the total length of the selected iso-contours' contour to the length of the round object contour (which is equal to iso-contours area ($S_{obj}=S_{circ}$); $k_{turb}=L_{obj}/L_{circ}$, where $k_{turb}$—degree of turbulence; $L_{obj}$—total length of the contour of studied iso-contours; $L_{circ}$—round object contour length; $S_{obj}$—area of studied iso-contour; $S_{circ}$—area of the equivalent round object. Application of this analysis method to differential frames, allows generating data on the extent of turbulent flow of biological fluids (especially blood in the heart and vessels).

A detailed description of the method is shown by the following clinical example.

Figure 16:
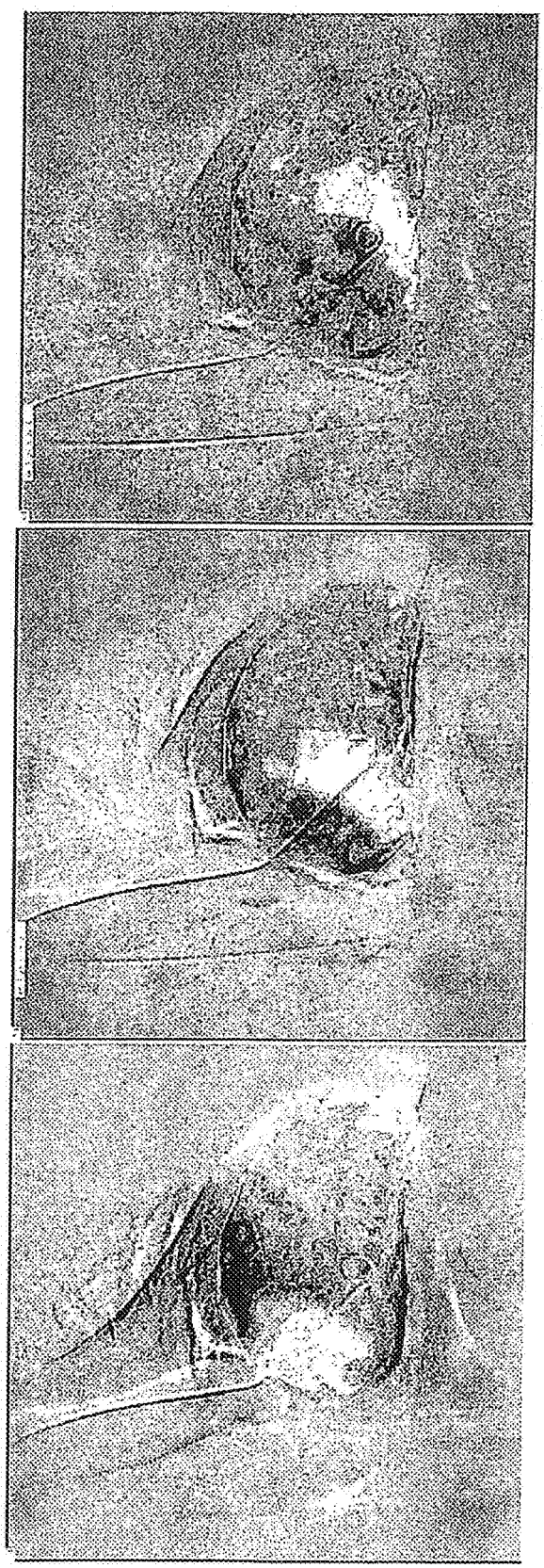
FIG. 16 shows a series of four iso-contours formed in three consecutive frames.

Patient G., 64 years old, was suffering from heart failure. Ventriculography was performed with differential frames created from initial frames and the release of blood promotion through the left ventricle. According to the described method, four iso-contours were created (two shades light and dark) (FIG. 16). Calculations of degrees of turbulence were made, for the middle frame shown in the table as shown in FIG. 17.

In the table, (Umax=10 and Umin=−10), i is the number of iso-contours, U is the cutoff level of brightness, L is the length of the contour boundary of the iso-contours [pixel count], S is the area covered by the iso-contours [pixel], k is $K_{turb}=L_{obj}/L_{circ}$, i.e. the ratio of the total length of the contour boundary L to the length of the circumference of a round object that has the same area S as the examined object. More particular, the relationship between L and S is as follows: If the radius of a round object is r, the area of the round object or $S_{circ}$ is $\pi \times r^2$. Accordingly $L_{circ}=2\pi \times r=$square root of $(4\pi \times S_{circ})$ or $3.54\times(S_{circ})^{1/2}$. For example, if S=1402, $L_{circ}=3.54\times(1402)^{1/2}=132.55$. With $L_{obj}=944$, $k_{turb}=944/132.55$ or approximately 7.11.

Figure 18A:
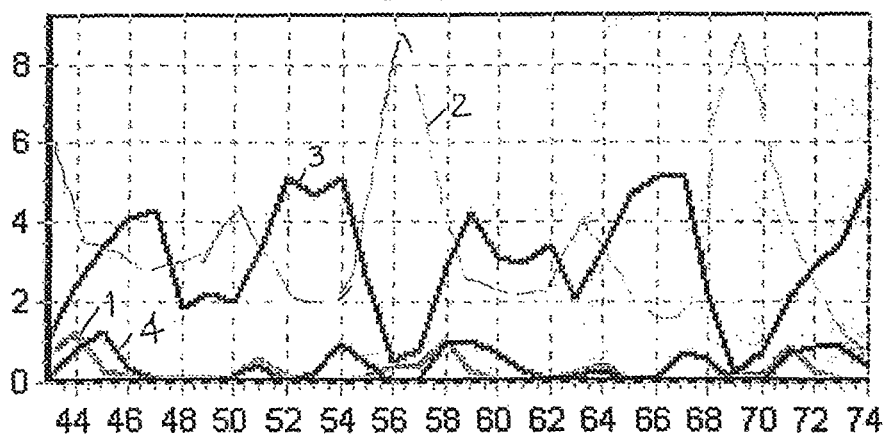
FIG. 18A-18C are the graphs showing the data (L, S and k) extracted by analysis of a series of consecutive frames.
Figure 18B:
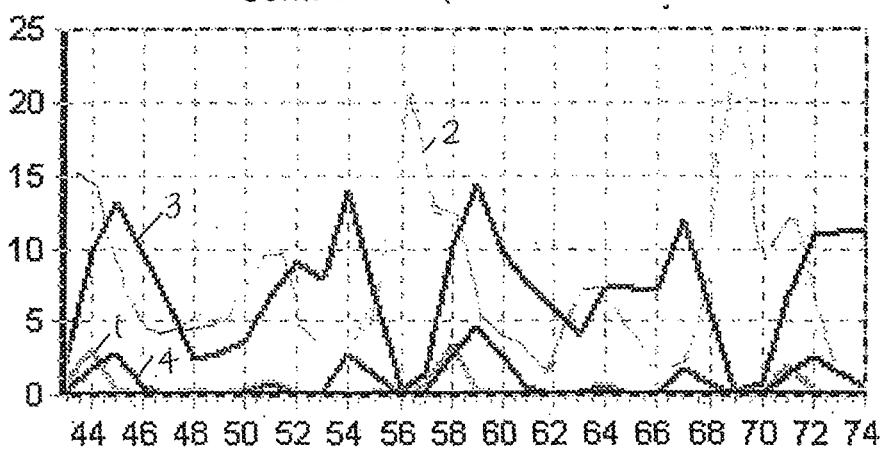
Figure 18C:
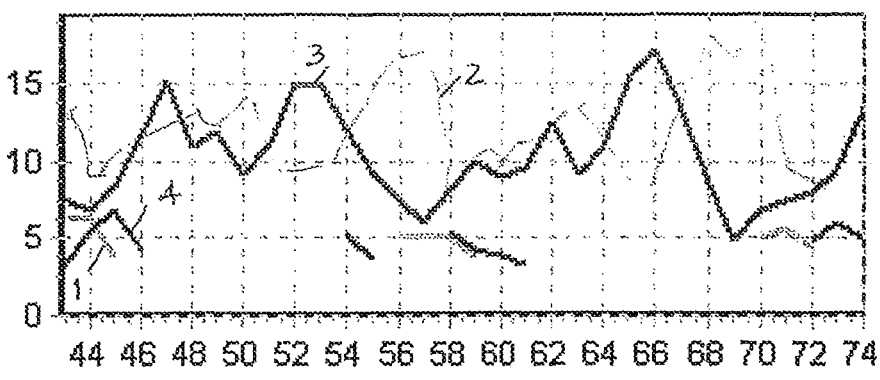

The above data (L, S and k), are extracted by analysis of a series of consecutive frames, which are shown in the three graphs of FIGS. 18A-18C.

The most interesting for generating a diagnosis are the minimum values of k for curves 3 and 4, corresponding to the upper "light" isocontours characterizing the movement of blood flowing in the ventricle through the mitral valve.

It was discovered that in a relatively healthy heart, $k_{turb}$ corresponds to two. In the case of a diseased heart, k increases to a from 4-6 or more.

It is important that in addition to assessing the degree of turbulence in some frames, it is useful to determine a rate of change or increase through a series of consecutive cardiac cycles.

Thus, the method allows generating an indicator of heart health using a computer based, non-invasive analysis that can give results based on a determination of a degree of turbulence during movement of biological fluids such as blood, which is particularly important for patients in whom a direct determination is not always possible.

Increased turbulence is associated with a likelihood of disease and may be used as both a diagnostic and prognostic criteria for predicting heart failure. The method involves an analysis of data from a contrast heart ventriculography, as well as other studies of the heart and vessels, primarily in nuclear magnetic resonance imaging, which does not require contrast and is quite noninvasive and in other branches of physiology and medicine associated with pulsating movement of biological fluids.

The computer based determination of a quantitative value for biological fluids movement turbulence, includes means for recording of digital electromagnetic images before and after a contrast agent is injected into the cavity of the organ, providing a computer program for comparing at least two digital frames and forming a film loop, wherein each frame is compared to a following frame, the program generating a differential frame obtained as a pixel by pixel brightness difference between the two consecutive frames, the computer based program assembling a series of differential frames into a film loop, with the difference in brightness optionally enhanced with the assistance of the contrast agent injected into the vessels that supply blood to the organ. The computer is configured to computer generate isocontours from the differential frames in the film loop as lines, limiting the areas of equal brightness to specific levels by creating five sublevels according to the formula $\Delta=(Umax-Umin)/4$, where Umax and Umin are the maximum and minimum brightness values, respectively. Extreme isocontours, which differ from Umax and Umin by a value of $\Delta/2$, are given priority in the analysis.

By creating iso-contours, a degree of turbulence can be calculated as the ratio of the total length of the chosen iso-contours to the length of a round object that has an area equivalent to the studied object ($S_{obj}=S_{circ}$) according to the formula; $k_{turb}=L_{obj}/L_{circ}$, where $k_{turb}$—degree of turbulence; $L_{obj}$—total length of the studied iso-contours; $L_{circ}$—round object contour length; $S_{obj}$—area of studied iso-contours, $S_{circ}$—area of the round object.

The present invention can be incorporated into a dedicated instrument for generating the images and data necessary for performing the differential analysis, or could be integrated as a dedicated computational software program/software module, and be incorporated into existing cardiac diagnostic equipment, such as an MRI, CT, EchoCG, angiography, etc.

It should be realized that the system shown in FIG. 1 can take different forms in actual hardware including hardware distributed in different locations. FIG. 1 thus shows an example of a system 10, according to an embodiment. The various processing modules may include at least one signal processor that includes at least one central processing unit and at least one memory device including a computer program that executes, at least in part, the processing described above. These processes may be expressed as a combination of computer instructions and data definitions that enable a computer such as a central processing unit to perform acts of computation or control. Thus, such instructions may take the form of software modules such as image and data processing modules as outlined in FIG. 1. Such software is sometimes referred to as comprising computer program code that likewise comprises computer instructions and data definitions expressed in a programming language or in a form output by an assembler, compiler, or other translator. A system comprising computer program code is thus able, together with at least one central processing unit, to cause the system at least to carry out certain process steps such as outlined in whole or in part above. The methods shown herein may be coded by a computer programmer so as to express method steps in a programming language.

The system could also be configured to remotely receive image data from the various pieces of diagnostic equipment, with the computations, analysis and turbulence level determination performed on a local computing device, accessible by the health care provider, instrument technician or another qualified individual. This is particularly advantageous as the system can utilize data and images currently available, and so does not require the patient to endure more or different procedures, and further remains a minimally invasive technique for generating a prognosis keyed to a unique quantitative heart function level based on a degree of blood turbulence.

Thus, research equipment records may exist in which a set of images or frames can be taken together to constitute a film which actually contains information about the dynamic processes that can be analyzed according to the present invention. The present invention permits the separate frames to be used to carry out the necessary differential image generation and analysis measurements. The differential image method provides a particular advantage as it provides a simple method for extracting static objects, such as bones, from the film, providing better visibility of moving objects with the aim of improving the visualization of these objects, consequently increasing the accuracy of the analysis.

Instead of attempting to make local calculations by freezing the original frames, the inventors have found that evaluating only the differences from frame to frame provides a more precise result with better resolution, a significant advance in the diagnostic arts.

Thus, although the present invention has been described with respect to one or more embodiments thereof, it will be understood by those skilled in the art that the foregoing and various other changes, omissions and deviations in the form and detail thereof may be made without departing from the scope of this invention.

What is claimed is:

1. A medical diagnostic system for a prognostic of cardiac function, comprising:
    an image storage device arranged to store medical images of a cardiovascular system, said medical images including consecutive images, the image storage device comprising stored as a plurality of image frames, the image frames arranged to store pixel-by-pixel brightness of the consecutive images;
    an image processing module arranged to generate one or more differential frames from the plurality of image frames;
    a data processing module configured to provide information indicative of blood flow in the cardiovascular system based at least partly on the differential frames, wherein the differential frames are generated based on the pixel-by-pixel brightness of the consecutive images, the image processing module also configured to generate a brightness segmentation image based on said one or more differential frames, and wherein the data processing module is configured to provide a turbulence index based on the brightness segmentation image, the turbulence index comprising the information indicative of blood flow in the cardiovascular system.

2. The medical diagnostic system according to claim 1, wherein the data processing module comprises a first data processor configured to compute a contour and an area of the brightness segmentation image, and a second data processor to compute the turbulence index based on the contour and the area of the brightness segmentation image.

3. A medical diagnostic system for a prognostic of cardiac function, comprising:
    an image storage device arranged to store medical images of a cardiovascular system, said medical images including consecutive images stored as a plurality of image frames, the image frames arranged to store pixel-by-pixel brightness of the consecutive images;
    an image processing module arranged to generate one or more differential frames from the plurality of image frames;
    a data processing module configured to provide information indicative of blood flow in the cardiovascular system based at least partly on the differential frames, wherein the image processing module is also configured to delineate wall of the cardiovascular system boundaries based on the differential frames, and the data processing module is also configured to generate information indicative of wall contraction-relaxation strength and synchronicity in the cardiovascular system.

4. The medical diagnostic system according to claim 3, wherein the image processing module is configured to delineate the wall of the cardiovascular system boundaries also cavity from walls and walls from cavity and surrounding structures in the cardiovascular system.

5. The medical diagnostic system according to claim 1, wherein the data processing module is arranged to provide the information to an information display to a user assessing the blood flow in the cardiovascular system according to the turbulence index.

6. The medical diagnostic system according to claim 1, wherein the image storage device is arranged to receive the medical images from a medical imaging device.

7. The medical diagnostic system according to claim 1, wherein the medical images comprise X-ray images.

8. The medical diagnostic system according to claim 1, wherein the medical images comprise computed tomography scan images.

9. The medical diagnostic system according to claim 1, wherein the medical images comprise magnetic resonance imaging images.

10. The medical diagnostic system according to claim 1, wherein the medical images comprise ultrasound images.

11. The medical diagnostic system according to claim 1, wherein the medical images comprise angiography images.

12. A method for generating a prognosis of cardiac function, comprising:
    administering a contrast agent into a cavity of a cardiovascular system;
    acquiring a plurality of consecutive images of the cardiovascular system;

generating a differential frame from at least two of the consecutive images; and providing information indicative of blood flow in the cardiovascular system based on the differential frame;

delineating wall boundaries of the cardiovascular system based on said information; and generating further information indicative of wall contraction-relaxation strength and synchronicity based on said delineating and differential frames analysis.

13. The method according to claim 12, further comprising:

generating a brightness segmentation image based on the differential frame;

determining a contour length and an area of the brightness segmentation image; and computing a turbulence index based on the contour length and the area for providing the information.

14. The method according to claim 13, wherein the turbulence index is computed from the ratio of the contour length of the brightness segmentation image to a circumference of a substantially circular loop having an area substantially equal to the area of the brightness segmentation image.

15. The method according to claim 12, wherein each of the images comprises a spatial distribution of pixel-by-pixel brightness levels and the differential frame is generated by comparing the spatial distribution of pixel-by-pixel brightness levels of said at least two of the images.

16. The method according to claim 15, wherein the differential frame comprises a range of brightness levels and wherein the range of brightness levels is segmented into a plurality of brightness zones including a max-brightness zone and a min-brightness zone, and wherein the brightness segmentation image is generated from the differential frame based on the plurality of brightness zones after removing the max-brightness zone and the min-brightness zone.

17. The medical diagnostic system according to claim 1, wherein the blood flow in the cardiovascular system comprises movement of blood flowing inside cardiac chambers including ventricles and valves.

18. The medical diagnostic system according to claim 1, wherein said medical images comprise images of a cavity of the cardiovascular system having a contrast agent administered in the cavity.

19. The medical diagnostic system according to claim 1, wherein the data processing module is configured to provide a turbulence index based on the brightness segmentation image of moving blood inside cardiac chambers.

20. The method according to claim 13, wherein the brightness segmentation image comprises brightness of the wall boundary of the cardiovascular system during one cardiac cycle for wall strength contraction-relaxation index and wall contraction-relaxation synchronicity index for generating prognosis of cardiac function.

* * * * *